United States Patent
Boime et al.

(10) Patent No.: US 6,693,074 B1
(45) Date of Patent: *Feb. 17, 2004

(54) CYSTINE DEPLETED GLYCOPROTEIN HORMONES

(75) Inventors: Irving Boime, St. Louis, MO (US); David Ben Menahem, St. Louis, MO (US)

(73) Assignee: Washington University, St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/933,693

(22) Filed: Sep. 19, 1997

(51) Int. Cl.⁷ .......................... A61K 38/24; A61K 38/22
(52) U.S. Cl. ........................ 514/8; 530/397; 530/398; 530/399
(58) Field of Search ................... 530/397, 398, 530/399; 514/8

(56) References Cited

FOREIGN PATENT DOCUMENTS

| WO | WO 95/22304 | | 8/1995 |
|---|---|---|---|
| WO | 96/05224 | * | 2/1996 |

OTHER PUBLICATIONS

Sugahara et al. Proceedings of the National Academy of Sciences of the United States of America, vol. 92, No. 6, pp. 2041–2045, Mar. 1995.*

Suganuma et al. J. Biol. Chem, 264:19302–19307, Oct. 1989.*

Sato et al. J. Biol. Chem, 272:18098–18103, Jul. 1997.*

Cystine Knot of the Gonadotropin α Subunit is Critical for Intracellular Behavior but Not for In Vitro Biological Activity, Asomi Sato, et al., *The Journal of Biological Chemistry*, 1997, vol. 272, No. 29 Issue of Jul. 18, pp 18098–18103 (1997).

The Biologic Action of Single–chain Choriogonadotropin Is Not Dependent on the Individual Disulfide Bonds of the β Subunit, David Ben–Menahem, et al., *The Journal of Biological Chemistry*, vol. 272, No. 11, Issue of Mar. 14, pp. 6827–6830 (1997).

Elimination of Di–Sulfide Bonds Affects Assembly and Secretion of the Human Chorionic Gonadotropin βSubunit, Nobuhiko Suganuma et al., *Journal of Biological Chemistry*, vol. 264, No. 32, Issue of Nov. 15, pp. 19302–19307 (1989).

Mutagenesis of cysteine Residues in the Human Gonadotropin αSubunit, Madoka Furuhashi, et al., *Journal of Biological Chemistry*, vol. 269, No. 41, Issue of Oct. 14, pp. 25543–25548 (1994).

Functional Expression of Yoked Human Chorionic Gonadotropin in Baculovirus–Infected Insect Cells, Prema Narayan, et al.,*Molecular Endocrinology*, vol. 9, No. 12, pp. 1720–1726 (1995).

* cited by examiner

*Primary Examiner*—Michael Borin
(74) *Attorney, Agent, or Firm*—Morrison & Foerster LLP

(57) ABSTRACT

Single-chain forms of the glycoprotein hormones LH, FSH, TSH or CG which are lacking at least one disulfide bridge in the sequence representing the α and/or β subunit are useful as agonists or antagonists of the native glycoprotein hormones.

17 Claims, 3 Drawing Sheets

CYSTINE DEPLETED GLYCOPROTEIN HORMONES

ACKNOWLEDGEMENT OF GOVERNMENT SUPPORT

This invention was made with government support under NIH Grant Nos. HD23398 and Hd92922, awarded by the National Institutes of Health. The U.S. Government has certain rights in this invention.

TECHNICAL FIELD

The invention relates to modified forms of single chain glycoprotein hormones wherein one or more cystine bonds in the α and/or β chain is disrupted. The cystine depleted forms are agonists or antagonists of the receptors for the relevant glycoprotein hormones.

BACKGROUND ART

The glycoprotein hormones, follicle stimulating hormone (FSH), luteinizing hormone (LH), thyroid stimulating hormone (TSH) and chorionic gonadotropin (CG) are heterodimers composed of an α subunit, which is identical for all four hormones in a particular species, and β subunits which differ within a species according to the identity of the hormone. These hormones are found in all mammals although chorionic gonadotropin has been determined as present only in primates and equine species. Each of the α and β subunits contain multiple cystine bridges which appear necessary to effect the proper conformation for dimerization and secretion.

Recently, single chain forms of these glycoprotein hormones have been disclosed. PCT Application at WO 96/05224 published Feb. 22, 1996, and PCT Application WO 95/22304 published Aug. 24, 1995, describe various single chain forms of these hormones and recombinant methods for their production. See also Sugahara, T. et al. *Proc Natl Acad Sci USA* (1995) 92:201–2045; Narayan, P. et al., *Mol Endocrinol* (1995) 9:172–1726. In these single chain forms, the α and β portions are provided as a single fusion protein, optionally containing a linker, wherein either the α or β is at the N-terminus.

Cysteine depleted mutants of the α and β subunits and of the heterodimers of some of the human glycoprotein hormones have been reported previously. It has been shown that chemical reduction or site specific mutations of individual cysteine residues in either the common α or β subunit alters dimer assembly and secretion rate. Suganuma, N. et al, *J Biol Chem* (1989) 264:19302–19307 and Furuhashi, M. et al, *J Biol Chem* (1994) 269:25543–25548. In the present work, it is shown that mutants lacking either the 7–31 or 59–87 bonds of the a subunit were secreted and that heterodimers containing the α 7–31 mutation bound to the LH/hCG receptor with comparable affinity to wild type hCG, whereas the α59–87 mutant interacted with lower binding affinity. Mutants comprising the cystine knot (10–60, 28–82 and 32–84) were not secreted in sufficient quantities to permit biological activity to be determined. The α7–31 and α59–87 forms had previously been prepared by Furuhashi, M., et a., supra.

Recently, the present applicant has reported the construction of βα single-chain forms of chorionic gonadotropin wherein, in each such form, one of the six cystine bridges normally present in the β subunit has been deleted. These cystine depleted forms are still able to bind to the appropriate receptor and stimulate the production of cyclic AMP. (Ben-Menahem D. etal, *J Biol Chem* (1997)272: 6827–6830). Similarly, the present applicant as shown that deletion of single cystine bridges in the α chain portion of this βα single chain hCG results in compounds with similar activity (Sato, A. et at., *J Biol Chem* (1997) 272:18098–18103).

The modified single-chain forms of the present invention provide additional members for the repertoire of agonists of the various heterodimeric glycoprotein hormones in various mammalian species and are useful as immunogens. Some members of this group may also act as antagonists.

DISCLOSURE OF THE INVENTION

Cystine bridge depleted single chain glycoprotein hormones derived from various species provide a new class of agonists (and antagonists) useful in enhancing (or inhibiting) fertility, modulating conditions associated with the reproductive system, and in the treatment of thyroid disorders. Enrichment of the resource of available agonists and antagonists provides added possibilities for treatment of individuals according to their unique metabolic and physiological profiles.

Thus, in one aspect, the invention is directed to a glycoprotein hormone agonist or antagonist which is a modified form of a glycoprotein hormone selected from the group consisting of follicle stimulating hormone (FSH), luteinizing hormone (LH), chorionic gonadotropin (CG) and thyroid stimulating hormone (TSH) of the formula:

$$\alpha\text{-(linker)}_n\text{-}\beta \qquad (1)$$

or $$(\beta)\text{-(linker)}_n\text{-}\alpha \qquad (2);$$

wherein β represents the β subunit of said FSH, LH, CG or TSH or a variant thereof; α represents the a subunit common to said glycoprotein hormones or a variant thereof; "linker" represents an amino acid sequence providing a fusion protein between the C-terminus of a and the N-terminus of β in formula (1) or the C-terminus of β and the N-terminus of α in formula (2); and n is 0 or 1; and wherein one or more cystine bridges contained in said α and/or β subunit is deleted.

In other aspects, the invention is directed to recombinant materials and methods for the production of the agonists and antagonists of the invention, to pharmaceutical compositions containing these compounds, and to methods to modify the metabolism or physiology of a subject using the modified hormones of the invention.

MODES OF CARRING OUT THE INVENTION

The invention provides a new class of agonists and antagonists which modulate the activity of receptors for LH, FSH, TSH and hCG. The ability of these single chain cystine depleted forms to behave as agonists and antagonists is surprising in view of the teachings of the art which demonstrate that cystine bridge deletion markedly affects the conformational structure of the hormones.

The availability of the single chain forms is particularly advantageous since any influence the deletion of cystine bridges may have on the ability of the subunits to form the heterodimer is overridden by their forced proximity.

The single chain agonists of the invention can be used therapeutically in a manner comparable to that of the heterodimeric forms of these hormones. Thus, these materials can be used in the treatment of infertility, as aids for in vitro fertilization techniques and in other therapeutic methods associated with the native hormones, both in humans and in animals. The antagonists, similarly, can be used to modulate the metabolic affects of inappropriate hormonal stimulation, such as hyperthyroidism in the case of antagonists to TSH and ovarian hyperstimulation in the case of the reproductive hormones. The agonists and antagonists are also used as diagnostic tools for detection of the presence or absence of antibodies with respect to the native proteins in biological samples and as control reagents in assay kits for assessing the levels of these hormones. Such diagnostic assessment is conducted using art known methods such as immunoassay methods involving fluorescent, enzyme, or radioisotope labels and using competitive or direct protocols. The antagonists and agonists are also useful in detecting and purifying receptors to which the native hormones bind, typically by coupling these materials to solid supports and conducting chromatographic separations. The receptors are themselves useful in assessing hormone activity for candidate drugs and in screening tests for therapeutic substances from libraries of candidates.

The compounds of the invention can also be used as immunogens for eliciting a cellular and/or humoral response. The response itself will affect the reproductive metabolism of the immunized subject. In addition antibodies uniquely reactive with the single chain modified forms of the hormones of the invention can be used as purification tools for isolation or preparation of these materials. By "uniquely reactive" is meant that the antibodies or immunospecific fragments thereof recognize these specific modified forms to the exclusion of the single chain forms, per se, the isolated subunit α or β chains or the heterodimeric forms.

Figure 1:
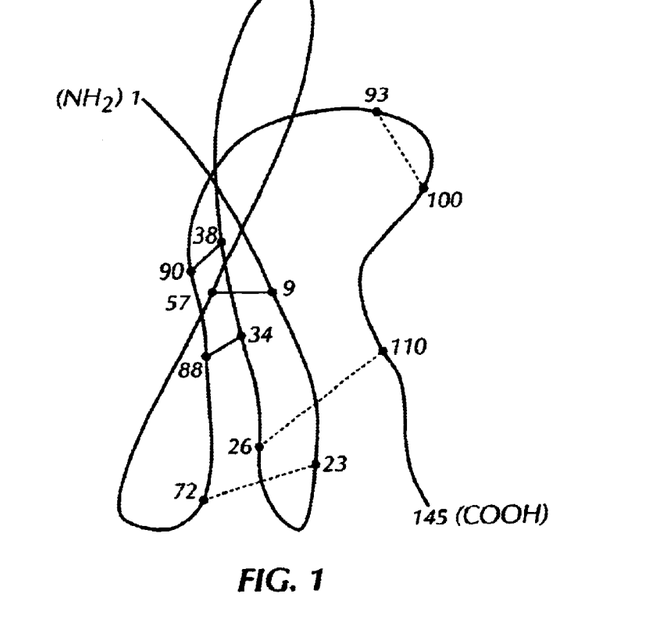
FIG. 1 is a schematic diagram of a proposed structure of the human CGβ subunit showing the deduced cystine bridge assignments.
Figure 2:
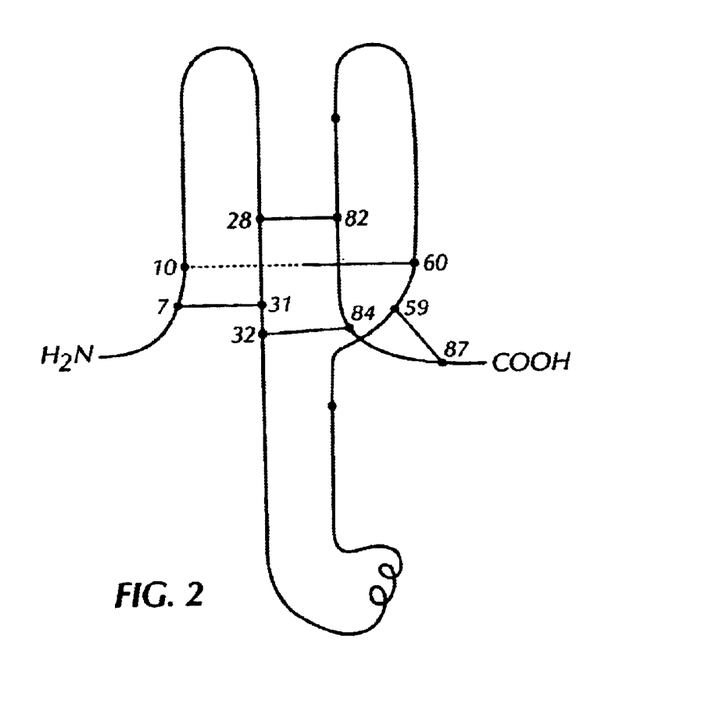
FIG. 2 shows a schematic proposed structure of the α subunit showing the location of the disulfide bridges.

The location of the disulfide bridges in the glycoprotein hormones is known or postulated. FIG. 1 shows the positions of these disulfide links in the β chains of hCG; FIG. 2 shows the position of these links in the human α subunit. With respect to the β chains of FSH, LH, and TSH, the cysteine residues are in conserved positions relative to their positions in chorionic gonadotropin (Pierce, J. G. et al. *Ann Rev Biochem* (1981) 50:465–495) and it is assumed that the cystine bridges are in analogous positions to those shown in FIG. 1 for hCG. The single chain forms of the invention are lacking at least one disulfide bridge. However, included within the invention are single chain forms where two or more disulfide bridges are lacking in either the α or β portion and where both the α and β portions are depleted of at least one disulfide bridge. In one embodiment of the invention, all of the disulfide bridges in the single chain form are lacking.

The α and β components of the single chain hormones of the invention refer to proteins having amino acid sequences known in the art per se or biologically active variants thereof regardless of glycosylation pattern. They are modified from native or variant forms only in the deletion of at least one cystine bridge in either the α or β chain. "Native" forms of these peptides are those which have the amino acid sequences isolated from the relevant mammalian tissue, and have these known sequences per se, or the sequences of their allelic variants.

"Variant" forms of these proteins are those which have deliberate alterations in the amino acid sequence of the native protein produced by, for example, site-specific mutagenesis or by other recombinant manipulations, or which are prepared synthetically.

These alterations consist of 1–10, preferably 1–8, and more preferably 1–5 amino acid changes, including deletions, insertions, and substitutions, most preferably conservative amino acid substitutions as defined below. The resulting variants must retain activity which affects the corresponding activity of the native hormone—i.e., either they must retain the biological activity of the native hormone directly, or they must behave as antagonists, generally by virtue of being able to bind the receptors for the native hormones, but lacking the ability to effect signal transduction.

One set of preferred variants are those wherein the glycosylation sites of either the α or β subunits or both have been altered. The α subunit contains two glycosylation sites, one at position 52 and the other at position 78. Similarly, the β subunits generally contain two N-linked glycosylation sites (at positions that vary somewhat with the nature of the β chain) and similar alterations can be made at these sites. The carboxy terminal peptide (CTP) extension present in hCG contains four O-linked glycosylation sites, and conservative mutations at the serine residues (e.g., conversion of the serine to alanine) destroys these sites. Destruction of the O-linked glycosylation sites may effect conversion of agonist activity to antagonist activity. Alterations in amino acid sequence that are proximal to the N-linked or O-linked glycosylation sites influence the nature of the glycosylation that is present on the resulting molecule and also alter activity.

Alterations in amino acid sequence also include both insertions and deletions.

Thus, truncated forms of the hormones are included among variants, e.g., mutants of the α subunit which are lacking some or all of the amino acids at positions 85–92 at the C-terminus. In addition, α subunits with 1–10 amino acids deleted from the N-terminus are included. Some useful variants of the hormone quartet described herein are set forth in U.S. Pat. No. 5,177,193 issued Jan. 5, 1993 and incorporated herein by reference. As shown therein, the glycosylation patterns can be altered by destroying the relevant sites or, in the alternative, by choice of host cell in which the protein is produced.

As explained above, the single chain forms are convenient starting materials for various engineered muteins. Such muteins include those with non-critical regions altered or removed. Such deletions and alterations may comprise entire loops, so that sequences of considerably more than 10 amino acids may be deleted or changed. The single chain molecules must, however, retain at least the receptor binding domains and/or the regions involved in signal transduction.

There is considerable literature on variants of the hormone quartet described herein and it is clear from this literature that a large number of possible variants which result both in agonists and antagonists activity can be prepared. Such variants are disclosed, for example, in Chen, F. et al. *Molec Endocrinol* (1992) 6:914–919; Yoo, J. et al. *J Biol Chem* (1993) 268:13034–13042; Yoo, J. et al. *J Biol*

*Chem* (1991) 266:17741–17743; Puett, D. et al. *Glycoprotein Hormones*, Lusbader, J. W. et al. EDS, *Springer Verlag* New York (1994) 122–134; Kuetmann, H. T. et al. (ibid) pages 103–117; Erickson, L. D. et al. *Endocrinology* (1990) 126:2555–2560; and Bielinska, M. et al. *J Cell Biol* (1990) 111:330a (Abstract 1844).

It has also been demonstrated that the β subunits of the hormone quartet can be constructed in chimeric forms so as to provide biological functions of both components of the chimera, or, in general, hormones of altered biological function. Thus, chimeric molecules which exhibit both FSH and LH/CG activities can be constructed as described by Moyle, *Proc Natl Acad Sci* (1991) 88:760–764; Moyle, *Nature* (1994) 368:251–255. As disclosed in these papers, substituting amino acids 101–109 of FSH-β for the corresponding residues in the CG-β subunit yields an analog with both hCG and FSH activity.

Although it is recognized that glycosylation pattern has a profound influence on activity, for convenience the terms FSH, LH, TSH, and CG and reference to their subunits denote the amino acid sequences characteristic of the peptides, regardless of glycosylation state.

As used herein "peptide" and "protein" are used interchangeably, since the length distinction between them is arbitrary.

In the single-chain forms of the present invention, the α and/or β chain may contain a CTP extension inserted into a noncritical region. "Noncritical" regions of the α and β subunits are those regions of the molecules not required for biological activity (including agonists and antagonists activity). In general, these regions are removed from binding sites, precursor cleavage sites, and catalytic regions. Regions critical for binding to receptors, or catalytic activity (for agonists) should be avoided. It should be noted that some of the regions which are critical in the case of the dimer become non-critical in the single chain forms since the restriction imposed by the single chain may obviate the necessity for these regions. The ascertainment of noncritical regions is readily accomplished by deleting or modifying candidate regions and conducting an appropriate assay for the desired activity. Regions where modifications result in loss of activity are critical; regions wherein the alteration results in the same or similar activity (including antagonists activity) are considered noncritical.

It is again emphasized, that by "biological activity" is meant activity which is either agnostic or antagonistic to that of the native hormones. Thus, certain regions are critical for behavior of a variant as an antagonists, even though the antagonists is unable to directly provide the physiological effect of the hormone.

For example, for the α subunit, positions 33–59 are thought to be necessary for signal transduction and the 20 amino acid stretch at the carboxy terminus is needed for signal transduction/receptor binding. Residues critical for assembly with the β subunit include at least residues 33–58, particularly 37–40.

Where the noncritical region is "proximal" to the N- or C-terminus, the insertion is at any location within 10 amino acids of the terminus, preferably within 5 amino acids, and most preferably at the terminus per se. In general, "proximal" is used to indicate a position which is within 10 amino acids, preferably within five amino acids, of a referent position, and most preferably at the referent position per se. Thus, certain variants may contain substitutions of amino acids "proximal" to a glycosylation site; the definition is relevant here. In addition, the α and β subunits may be linked to each other at positions "proximal" to their N- or C-termini.

As used herein, the "CTP unit" refers to an amino acid sequence found at the carboxy terminus of human chorionic gonadotropin β subunit which extends from amino acid 112–118 to residue 145 at the C-terminus or to a portion thereof. Thus, each "complete" CTP unit contains 28–34 amino acids, depending on the N-terminus of the CTP. Each CTP unit may be complete or a fragment, and native or a variant. All of the CTP units in a tandem extension or insert may be identical, or they may be different from each other.

The "linker moiety" is a moiety that joins the α and β sequences without interfering with the activity that would otherwise be exhibited by the same α and β chains as members of a heterodimer, or which alters that activity to convert it from agonist to antagonist activity. The level of activity may change within a reasonable range, but the presence of the linker cannot be such so as to deprive the single-chain form of both substantial agonist and substantial antagonist activity. The single-chain form must remain as a single-chain form when it is recovered from its production medium and must exhibit activity pertinent to the hormonal activity of the heterodimer, the elements of which form its components.

It should be understood that in discussing linkages between the termini of the subunits comprising the single chain forms, one or more termini may be altered by substitution and/or deletion as described above.

Variants

The hormone subunits and the CTP units may correspond exactly to the native hormone or CTP sequence, or may be variants. The nature of the variants has been defined hereinabove. In such variants, 1–10, preferably 1–8, and most preferably 1–5 of the amino acids contained in the native sequence are substituted by a different amino acid compared to the native amino acid at that position, or 1–10, more preferably 1–8 and most preferably 1–5 amino acids are simply deleted or combination of these. As pointed out above, when non-critical regions of the single chain forms are identified, in particular, through detecting the presence of non-critical "loops", the number of amino acids altered by deletion or substitution may be increased to 20 or 30 or any arbitrary number depending on the length of amino acid sequence in the relevant non-critical region. Of course, deletion or substitutions in more than one non-critical region results in still greater numbers of amino acids in the single chain forms being affected and substitution and deletions strategies may be used in combination. The substitutions or deletions taken cumulatively do not result in substantial elimination of agonists or antagonists activity associated with the hormone. Substitutions by conservative analogs of the native amino acid are preferred.

"Conservative analog" means, in the conventional sense, an analog wherein the residue substituted is of the same general amino acid category as that for which substitution is made. Amino acids have been classified into such groups, as is understood in the art, by, for example, Dayhoff, M. et al., *Atlas of Protein Sequences and Structure* (1972) 5:89–99. In general, acidic amino acids fall into one group; basic amino acids into another; neutral hydrophilic amino acids into another; and so forth.

If the single-chain proteins of the invention are constructed by recombinant methods, they will contain only gene encoded amino acid substitutions; however, if any portion is synthesized by standard, for example, solid phase, peptide synthesis methods and ligated, for example, enzymatically, into the remaining protein, non-gene encoded amino acids, such as aminoisobutyric acid (Aib), phenylglycine (Phg), and the like can also be substituted for their analogous counterparts.

These non-encoded amino acids also include, for example, β-alanine (β-Ala), or other omega-amino acids, such as 3-amino propionic, 4-amino butyric and so forth, sarcosine (Sar), ornithine (Orn), citrulline (Cit), t-butylalanine (t-BuA), t-butylglycine (t-BuG), N-methylisoleucine (N-MeIle), and cyclohexylalanine (Cha), norleucine (Nle), cysteic acid (Cya) 2-naphthylalanine (2-Nal); 1,2,3,4-tetrahydroisoquinoline-3-carboxylic acid (Tic); mercaptovaleric acid (Mvl); J-2-thienylalanine (Thi); and methionine sulfoxide (MSO). These also fall conveniently into particular categories of conservative substituents analogous to the gene encoded amino acids.

Preferred Embodiments

The single-chain hormones of the invention are most efficiently and economically produced using recombinant techniques. Therefore, those forms of α and β chains, CTP units and other linker moieties which include only gene-encoded amino acids are preferred. It is possible, however, as set forth above, to construct at least portions of the single-chain hormones using synthetic peptide techniques or other organic synthesis techniques and therefore variants which contain nongene-encoded amino acids are also within the scope of the invention.

CTP units are preferred inclusions in the linker moiety. However, the linker may generally be a peptide comprising an arbitrary number, but typically less than 100, more preferably less than 50 amino acids which has the proper hydrophilicity/hydrophobicity ratio to provide the appropriate spacing and conformation in solution. In general, the linker should be on balance hydrophilic so as to reside in the surrounding solution and out of the way of the interaction between the α and β subunits. It is preferable that the linker include β turns typically provided by proline residues.

Preferred Embodiments of the α and β Subunits

As the unmodified forms from which at least one cystine bridge is deleted, the native forms of the α and β subunits in the single-chain form are among the preferred embodiments. However, certain variants are also preferred.

In particular, variants of the α subunit in which the N-linked glycosylation site at position 52 is eliminated or altered by amino acid substitutions at or proximal to this site are preferred for antagonists activity. Similar modifications at the glycosylation site at position 78 are also preferred. Deletion of one or more amino acids at positions 85–92 also affects the nature of the activity of hormones containing the α subunit and substitution or deletion of amino acids at these positions is also among the preferred embodiments.

Similarly, the N-linked glycosylation sites in the β chain can conveniently be modified to eliminate glycosylation and thus affect the agonists or antagonists activity of the β chains. If CTP is present, either natively as in CG or by virtue of being present as a linker, the O-linked glycosylation sites in this moiety may also be altered.

Particular variants containing modified or deleted glycosylation sites are set forth in Yoo, J. et al. *J Biol Chem* (1993) 268:13034–13042; Yoo, J. et al. *J Biol Chem* (1991) 266:17741–17743; and Bielinska, M. et al. *J Cell Biol* (1990) 111:330a (all cited above) and in Matzuk, M. M. et al. *J Biol Chem* (1989) 264:2409–2414; Keene, J. L. et al. *J Biol Chem* (1989) 264:4769–4775; and Keene, J. L. et al. *Mol Endocrinol* (1989) 3:2011–2017.

Not only may the glycosylation sites per se be modified directly, but positions proximal to these sites are preferentially modified so that the glycosylation status of the mutant will be affected. For the α subunit, for example, variants in which amino acids between positions 50–60 are substituted, including both conservative and nonconservative substitutions, are favored, especially substitutions at positions 51, 53 and 55 because of their proximity to the glycosylation site at $Asn_{52}$.

Also preferred are mutants of the α subunit wherein lysine at position 91 is converted to methionine or glutamic acid.

Although the variants have been discussed in terms of variations in the individual subunits hereinabove, it will be recalled that the single chain forms of the dimer offer additional opportunities for modification. Specifically, regions that are critical to folding of the dimer may not be critical to the correct conformation of the single chain molecule and these regions are available for variation in the single chain form, although not described above in terms of individual members of the dimeric forms. Further, the single chain forms may be modified dramatically in the context of non-critical regions whose alteration and/or deletion do not affect the biological activity as described above.

Preferred are forms of the compounds of the invention wherein the β subunit is at the N-terminus—i e., embodiments of formula 2. Also preferred are embodiments wherein the cystine bridge is deleted by substituting for both cysteine residues a similar amino acid, such as alanine serial, or glycine, preferably alanine. Also preferred are embodiments wherein, in the β chain of human chorionic gonadotropin, at least one disulfide link selected from the group consisting of 9–57, 23–72, 93–100, and 26–110 is deleted, but the cystine bridges at positions 34–88 and 38–90 are left intact. Also preferred are embodiments wherein all cystine bridges of the β subunit of any of the glycoprotein hormones are deleted. Preferred with regard to cystine bridge deletions in the α subunit are those wherein at least one cystine bridge at positions 7–31, 10–60, 28–82 or 32–84 is deleted, but that at position 59–87 is left intact. Also preferred are embodiments wherein all cystine bridges are deleted, including embodiments wherein both α and β subunits contain at least one cystine bridge deletion and those wherein all cystine bridges in the single chain hormone are deleted.

In the discussion above, the α and β subunits may either be native forms or variants.

Other Modifications

The proteins of the invention may be further conjugated or derivatized in ways generally understood to derivatize amino acid sequences, such as phosphorylation, glycosylation, deglycosylation of ordinarily glycosylated forms, modification of the amino acid side chains (e.g., conversion of proline to hydroxyproline) and similar modifications analogous to those post-translational events which have been found to occur generally.

As is generally known in the art, the single-chain proteins of the invention may also be coupled to labels, carriers, solid supports, and the like, depending on the desired application. The labeled forms may be used to track their metabolic fate; suitable labels for this purpose include, especially, radioisotope labels such as iodine 131, technetium 99, indium 111, and the like. The labels may also be used to mediate detection of the single-chain proteins in assay systems; in this instance, radioisotopes may also be used as well as enzyme labels, fluorescent labels, chromogenic labels, and the like. The use of such labels is particularly helpful for these proteins since they are targeting agents receptor ligand.

The proteins of the invention may also be coupled to carriers to enhance their immunogenicity in the preparation of antibodies specifically immunoreactive with these new modified forms. Suitable carriers for this purpose include keyhole limpet hemocyanin (KLH), bovine serum albumin (BSA) and diphtheria toxoid, and the like. Standard coupling techniques for linking the modified peptides of the invention to carriers, including the use of bifunctional linkers, can be employed.

Similar linking techniques, along with others, may be employed to couple the proteins of the invention to solid supports. When coupled, these proteins can then be used as affinity reagents for the separation of desired components with which specific reaction is exhibited.

Preparation Methods

Methods to construct the proteins of the invention are well known in the art. As set forth above, if only gene encoded amino acids are included the most practical approach at present is to synthesize these materials recombinantly by expression of the nucleotide sequence encoding the desired protein. DNA containing the nucleotide sequence encoding the single-chain forms, including variants, can be prepared from native sequences. Thus, the deletion of the cystine bridge can readily be accomplished by mutating the nucleotide sequence encoding the native or variant form used as a basis. Alternatively, the desired nucleotide sequence containing the required modification can be synthesized de novo. Of course, various segments of nucleotide sequence can be manipulated, thus replacing a portion of the sequence already containing a desired modification in lieu of an unmodified sequence suitably bracketed by restriction sites. Techniques for site-directed mutagenesis, ligation of additional sequences, PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the coding sequences. As is well known, expression systems are now available compatible with a wide variety of hosts, including procaryotic hosts such as bacteria and eucaryotic hosts such as yeast, plant cells, insect cells, mammalian cells, avian cells, and the like.

The choice of host is particularly to posttranslational events, most particularly including glycosylation. The location of glycosylation is mostly controlled by the nature of the glycosylation sites within the molecule; however, the nature of the sugars occupying this site is largely controlled by the nature of the host. Accordingly, a fine-tuning of the properties of the hormones of the invention can be achieved by proper choice of host.

A particularly preferred form of gene for the α subunit portion, whether the α subunit is modified or unmodified, is the "minigene" construction described by Matzuk, M. M., et al, *Mol Endocrinol* (1988) 2:95–100.

For recombinant production, modified host cells using expression systems are used and cultured to produce the desired protein. These terms are used herein as follows:

A "modified" recombinant host cell, i.e., a cell "modified to contain" with the recombinant expression systems of the invention, refers to a host cell which has been altered to contain this expression system by any convenient manner of introducing it, including transfection, viral infection, and so forth. "Modified" refers to cells containing this expression system whether the system is integrated into the chromosome or is extrachromosomal. The "modified" cells may either be stable with respect to inclusion of the expression system or not. In short, "modified" recombinant host cells with the expression system of the invention refers to cells which include this expression system as a result of their manipulation to include it, when they natively do not, regardless of the manner of effecting this incorporation.

"Expression system" refers to a DNA molecule which includes a coding nucleotide sequence to be expressed and those accompanying control sequences necessary to effect the expression of the coding sequence. Typically, these controls include a promoter, termination regulating sequences, and, in some cases, an operator or other mechanism to regulate expression. The control sequences are those which are designed to be functional in a particular target recombinant host cell and therefore the host cell must be chosen so as to be compatible with the control sequences in the constructed expression system.

If secretion of the protein produced is desired, additional nucleotide sequences encoding a signal peptide are also included so as to produce the signal peptide operably linked to the desired single-chain hormone to produce the preprotein. Upon secretion, the signal peptide is cleaved to release the mature single-chain hormone.

As used herein "cells," "cell cultures," and "cell lines" are used interchangeably without particular attention to nuances of meaning. Where the distinction between them is important, it will be clear from the context. Where any can be meant, all are intended to be included.

The protein produced may be recovered from the lysate of the cells if produced intracellularly, or from the medium if secreted. Techniques for recovering recombinant proteins from cell cultures are well understood in the art, and these proteins can be purified using known techniques such as chromatography, gel electrophoresis, selective precipitation, and the like.

All or a portion of the hormones of the invention may be synthesized directly using peptide synthesis techniques known in the art.

Antibodies

The proteins of the invention may be used to generate antibodies specifically immunoreactive with these new compounds. By "specifically immunoreactive" is meant that the antibodies or their relevant antigen binding fragments bind only to the compounds of the invention and not to related compounds such as individual subunits, heterodimers, or single chain forms which lack the deletion of at least one cystine bridge. These antibodies are useful in a variety of diagnostic and therapeutic applications. For example, when the single-chain forms of the invention are used therapeutically in either human or veterinary contexts, the levels of drug may be monitored using these antibodies using conventional immunoassay techniques.

The antibodies are generally prepared using standard immunization protocols in mammals such as rabbits, mice, sheep or rats, and the antibodies are titered as polyclonal antisera to assure adequate immunization. The polyclonal antisera can then be harvested as such for use in, for example, immunoassays. Antibody-secreting cells from the host, such as spleen cells, or peripheral blood leukocytes, may be immortalized using known techniques and screened for production of monoclonal antibodies immunospecific with the proteins of the invention. To obtain antibodies that are specifically immunoreactive with these compounds, cells producing monoclonal antibodies are tested for reactivity both with the desired compound of the invention and with related single chain compounds lacking the cystine bridge deletion. Those which react with the unmodified cystine bridge-containing form are discarded.

Formulation

The proteins of the invention are formulated and administered using methods comparable to those known for the corresponding heterodimers. Thus, formulation and administration methods will vary according to the particular hormone used. However, the dosage level and frequency of administration may be altered as compared to the heterodimer, especially if CTP units are present in view of the extended biological half life due to its presence.

Formulations for proteins of the invention are those typical of protein or peptide drugs such as found in *Remington's Pharmaceutical Sciences*, latest edition, Mack Publishing Company, Easton, Pa. Generally, proteins are administered by injection, typically intravenous, intramuscular, subcutaneous, or intraperitoneal injection, or using formulations for transmucosal or transdermal delivery. These formulations generally include a detergent or penetrant such as bile salts, fusidic acids, and the like. These formulations can be administered as aerosols or suppositories or, in the case of transdermal administration, in the form of skin patches.

Oral administration is also possible provided the formulation protects the peptides of the invention from degradation in the digestive system.

Optimization of dosage regimen and formulation is conducted as a routine matter and as generally performed in the art.

Methods of Use

As set forth above, the hormones of the invention may be used in many ways, most evidently as substitutes for the heterodimeric forms of the hormones or as antagonists. Because the compounds of the invention provide additional embodiments of agonists and antagonists, therapy may be fine tuned to the individual treated.

The following examples are intended to illustrate but not to limit the invention.

EXAMPLE 1

Preparation of CGβα Mutants with β Subunit Deletions

A KpnI-XhoI 2.7 kilobase fragment containing single-chain hCG, (CGβα) in vector pM²HA (Sugahara, T et al., *Proc Natl Acad Sci USA* (1995) 92: 2041–2045) was substituted into pBluescript II KS (Strategene). Various modifications have previously been made in the nucleotide sequence encoding the 1 chain of human CG to replace the cysteine residue at each location with an alanine residue, as described by Suganuma, N., et al., *J Biol Chem* (1989) 264: 19302–19307. For the relevant substitutions, the ApaI fragment containing the first 135 amino acids of the CGβ sequence in CGβα was exchanged for the ApaI fragment in the appropriate CGβΔCys of Suganuma, N., et al. supra. The resulting KpnI-XhoI fragment was inserted into pM²AH and rechecked by restriction enzyme analysis. Mutations were confirmed using the Taq DyeDeoxy Terminator Cycle Sequencing Kit and an ABI prism DNA Sequencer (Perkin Elmer).

The appropriate vectors were transformed into Chinese hamster ovary (CHO) cells and maintained as described in Suganuma, N., et al., and Sugahara, et al. supra. Individual clones producing the modified cystine bridge depleted forms were used to produce the desired proteins, which were secreted into the medium. The conditioned medium from cells grown in serum-free F12 was concentrated using Amicon Centriprep 10 concentrators and the concentrate was diluted 1:15 in phosphate-buffered saline, and the volume reduced again. The secreted protein was quantitated using polyclonal α antiserum in double antibody RIA (Diagnostic Products Corp.).

The transfected CHO cells stably expressing the disulfide deleted mutants were labeled with 25 μCi/ml Pro-mix (Amersham) for 4 hours and lysate and medium were subjected to SDS-polyacrylamide gel electrophoresis under reduced conditions and precipitated with antiserum. In the case of the β subunit per se, antiserum to the β subunit was used; for the single-chain forms, antiserum to the α subunit was used; and for precipitation of the heterodimer, antiserum either to the α or β subunit was used. The secretion kinetics were calculated with the results shown in Table 1 where $t_{1/2}$ represents the time when half the maximal secreted hormone is detected in the medium. The "recovery" is expressed as the amount of hormone retrieved from the medium at a steady state as a fraction of the total (lysate plus medium). For kinetic determinations, the cells were labeled for 16 hours with $^{35}$S-labeled cysteine, and equal aliquots of lysate and media immunoprecipitated with α- or CGβ antisera. Table 1 also shows the secretion rate of β subunit modified to delete disulfide bridges in a manner corresponding to the single-chain form. The values that bear an asterisk are those published by Sugahara, et al. supra.

TABLE 1

Secretion of hCGβ Cystine-Depleted Mutants
Results are expressed as mean ± S.E. of 3–6 experiments.

| | Secretion rate (t½) | | Recovery | |
|---|---|---|---|---|
| Hormone | Single-chain | βSubunit | Single-chain | Heterodimer |
| | min | | % | |
| WT | 86 ± 7 | 150* | 76 ± 5 | >80 |
| 34–88 | 351 ± 38 | 320* | 24 ± 3 | 4 ± 1 |
| 38–90 | 158 ± 9 | 200 | 55 ± 4 | <1 |
| 9–57 | 173 ± 24 | 220 | 39 ± 15 | 7 ± 1 |
| 23–72 | 105 ± 5 | 180* | 47 ± 4 | 22 ± 4 |
| 93–100 | 149 ± 11 | 170* | 71 ± 8 | <1 |
| 26–110 | 59 ± 7 | 34* | 89 ± 4 | 9 ± 4 |

EXAMPLE 2

Biological Activity of CGβα Cystine Depleted Mutants

A kidney-derived cell line (293) stably transfected with the cDNA encoding human LH/CG receptor, was used to determine receptor binding and cAMP production. This cell line is described by Jia, X-C et al., *Mol Endocrinol*, (1991) 5: 759–768. In this determination, the concentration of the compound to be tested in conditioned media from the CHO cells was determined by RIA and displacement curves of 125-hCG were obtained by determining at each dose of unlabeled hormone the percentage of maximum binding of the tracer. Adenylate cyclase activity was determined by RIA.

Figure 3A:
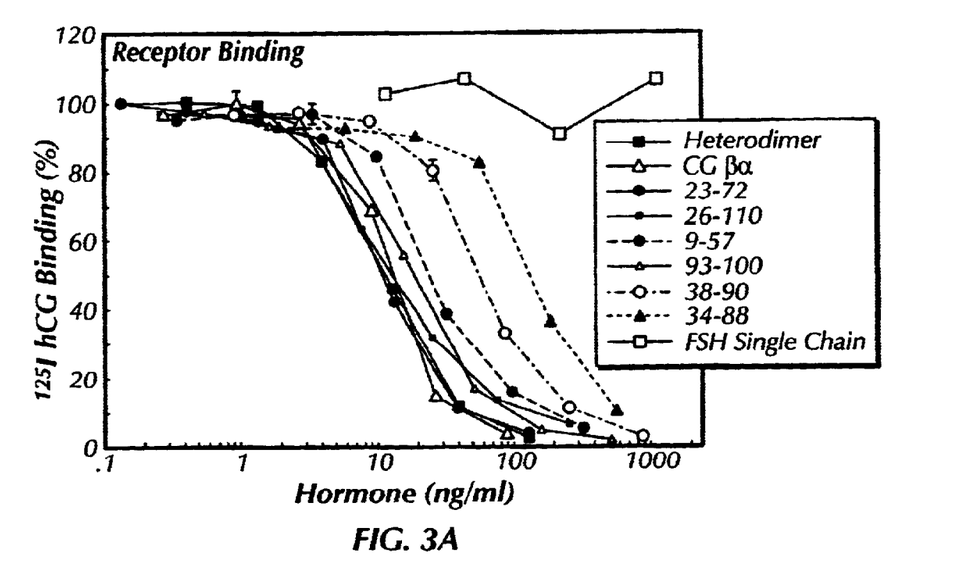
FIGS. 3a and 3b are graphical representations of the receptor binding activity and signal transduction activity of various CGβα single chain cystine bridge depleted forms containing deletions of disulfide bridges in the β subunit.
Figure 3B:
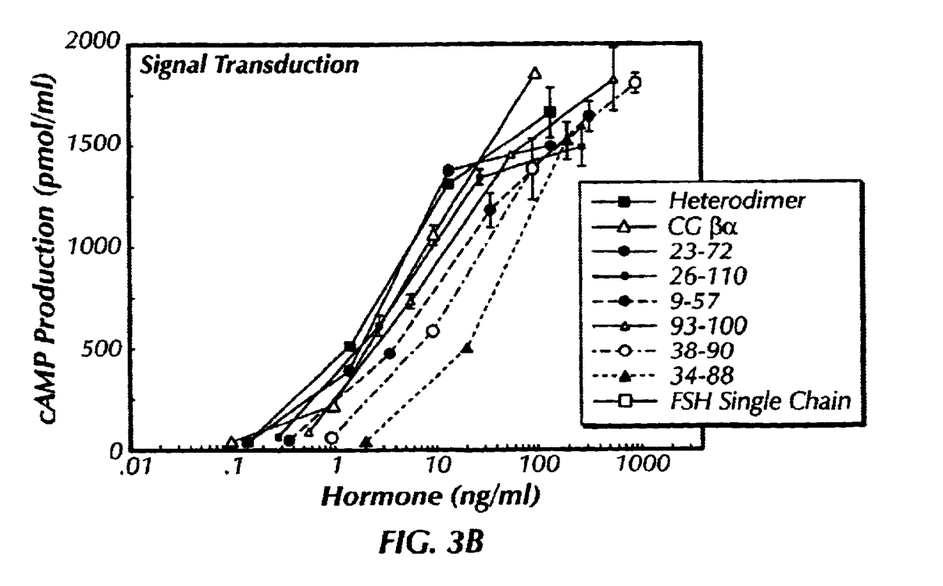

The results are shown in FIGS. 3a (binding) and 3b (signal transduction).

All of the CG variants bound to the receptor, including mutants wherein the subunits assemble poorly. The mutants, except for analogs β38–90 and β34–88, displayed similar dose response curves compared to the purified heterodimer, CR129 provided by the National Hormone and Pituitary Agency and to CGβα without cystine depletion. The results are set forth in Table 2 where $IC_{50}$ and $EC_{50}$ define the hormone concentration in ng/ml at 50% displacement of the tracer and half maximal cAMP stimulation, respectively. The results shown are from 2–4 experiments and are shown as mean±S.E. Each is conducted in duplicate.

TABLE 2

Biological Activity of β-Subunit Cystine-Depleted Mutants

| Hormone | Binding $IC_{50}$ | cAMP $EC_{50}$ | Coupling factor ($IC_{50}/EC_{50}$) |
|---|---|---|---|
| Heterodimer | 9.5 ± 2.4 | 4.5 ± 0.6 | 2.1 |
| CGβα | 10.3 ± 2.1 | 4.6 ± 1.6 | 2.2 |
| 34–88 | 93 ± 24 | 32 ± 5 | 2.9 |
| 38–90 | 67 ± 11 | 51 ± 21 | 1.3 |
| 9–57 | 20 ± 4 | 13 ± 1 | 1.5 |
| 23–72 | 8.0 ± 2 | 5.0 ± 2 | 1.6 |
| 93–100 | 15 ± 4 | 13 ± 2.4 | 1.2 |
| 26–110 | 23 ± 6 | 9.1 ± 4.5 | 2.5 |

The data show that bioactivity was preserved in these mutants.

EXAMPLE 3

Prepaation of CGβα With α Subunit Deletions

The previously constructed cysteine depleted mutants contained in vector $pM^2$ described in Furuhashi, M., et al, *J Biol Chem* (1994) 269: 25543–25548, cited above, were used. Exxon III of the α subunit contains a unique XbaI restriction site at residues 34–35; the vector also contains a single XhaI site so that fragments containing α10, α28, or α32 mutations were exchanged with XbaI digested $pM^2$ containing either α60, α82, or α84 mutations to obtain double cysteine mutants α10–60, α28–82 and α32–84 respectively. Construction of the double cysteine mutants α7–31 and α59–87 in $pM^2$ was previously described.

The single chain forms of these mutants were constructed with the carboxyl end of the β subunit fused to the amino end of the α subunit using overlapping PCR mutagenesis as described by Sugahara, T. et al. *Proc Natl Acad Sci USA* (1995) 92:2041–2045, cited above. The resulting constructs were sequenced for confirmation. Transduction, selection of stable of stable CHO clones, metabolic labeling, immunoprecipitation with subunit specific antiserum and analysis by Western blot were performed as described in Example 1 herein.

The ability of CHO cells to secrete the cystine mutants effectively, either as heterodimers as predicted by previous work, or as the single chain form, was tested with labeled cysteine and pulse-chase analysis. Both lysate and media were immunoprecipitated and resolved on SDS gels to determine $t_{1/2}$—i.e. the time when ½ maximal signal is detected in the medium, and to determine the percent recovery which is the fraction of the total recombinant protein produced found in the medium. The results are shown in Table 3.

TABLE 3

Secretion of a Subunit Cystine-Depleted Mutants

| | Monomer | | Dimer | Single-Chains | |
|---|---|---|---|---|---|
| Variant | t½ (min) | Recovery (%) | Recovery (%) | t1/2 (min) | Recovery (%) |
| aWT | 130 ± 12 | 92 ± 4 | 83 ± 1 | | |
| CGβα | | | | 106 ± 4 | 74 ± 5 |
| 7–31 | 135 ± 18* | >95* | 77 ± 6 | 107 ± 5 | 81 ± 5 |
| 10–60 | 195 ± 34 | 21 ± 6 | <5 | 244 ± 36 | 36 ± 3 |
| 28–82 | 123 ± 30 | 41 ± 6 | 49 ± 5 | 102 ± 15 | 55 ± 5 |
| 32–84 | 114 ± 6 | 20 ± 4. | <5 | 138 ± 32 | 45 ± 6 |
| 59–87 | 142 ± 36* | >95* | 90 ± 5 | 102 ± 13 | 87 ± 4 |

The asterisked data were determined in a previous study.

As shown in Table 3, all of the single chain cystine depleted mutants were recovered from the medium in significant amounts. The comparatively low recoveries of the monomer subunits of α10–60, α28–82 and α32–84 was not due to lower synthesis, but to enhanced degradation since at zero time of chase the intracellular accumulations of the mutants is comparable.

To obtain comparative data for secretion of the heterodimer, the α containing constructs were cotransfected with the hCGβ gene (Matzuk, M. M., et al., *J Cell Biol* (1988) 106:1049–1059) and clones synthesizing excess β subunit were selected so that the availability of β subunit would not limit formation of the dimer. As shown in Table 3, α10–60 and α32–84 dimers were even more poorly secreted than the monomers although synthesis was at a significant level. For α28–82, it was shown that the dimer formation was not affected by the depletion of the cystine bridge since amounts of dimer precipitated by either α or β subunit antiserum were comparable. Pulse-chase experiments also show that the α7–31, α28–82 and α59–87 mutants combined efficiently with the β subunit.

It appears that the disulfide bonds α10–60 and α32–84, and to a lesser extent α28–82 are critical for assembly. If the β and α subunits were covalently linked (Table 3), although the percent recovery was still diminished when one of the bridges in the cystine knot was deleted, significant amounts of these forms were secreted into the medium, thus permitting assessment of biological activity. The advantage of the single chain forms is clearly seen here, where the negative impact of cystine depletion on assembly is effectively overcome.

Significant changes in conformation were shown for the α10–60 and α32–84 mutants as demonstrated by probing Western blots obtained using conditioned media from cells producing these mutants. Two dimer-specific monoclonal antibodies, A407 and B109 were used as probes. A407 has an epitope in amino acid residues 5–6/11/13/81 of the α subunit (see FIG. 2) and is described by Moyle, W. R. et al, *J Biol Chem* (1995)270:20020–20031. This antibody recognizes, under non-reducing conditions, the non-mutated single chain and heterodimeric forms in all of the above-described cystine depleted mutants except α10/60 and α32–84. In addition, the migration of these mutants is altered.

Similarly, B109 which is specific for the dimer form of the subunit β fails to recognize either the α10–60 or the α32–84 mutants in the single chain form. Thus, these mutants, in particular, have altered conformations from the native hormones.

EXAMPLE 4

Biological Activity of the CGβα Cystine Mutants of the α Subunit

Figure 4A:
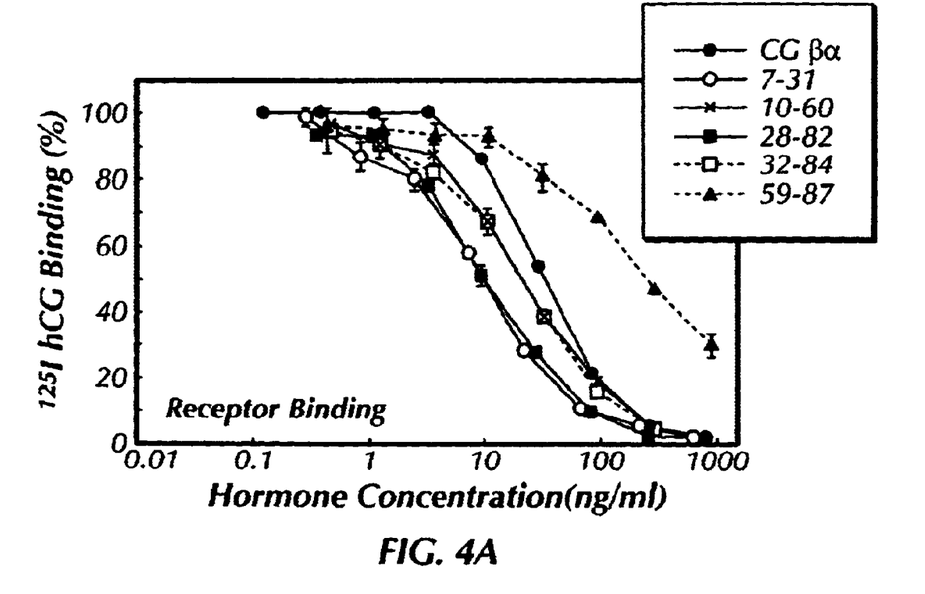
FIGS. 4a and 4b are graphical representations of the receptor binding activity and signal transduction activity of various CGβα single chain cystine bridge depleted forms containing deletions of disulfide bridges in the α subunit.
Figure 4B:
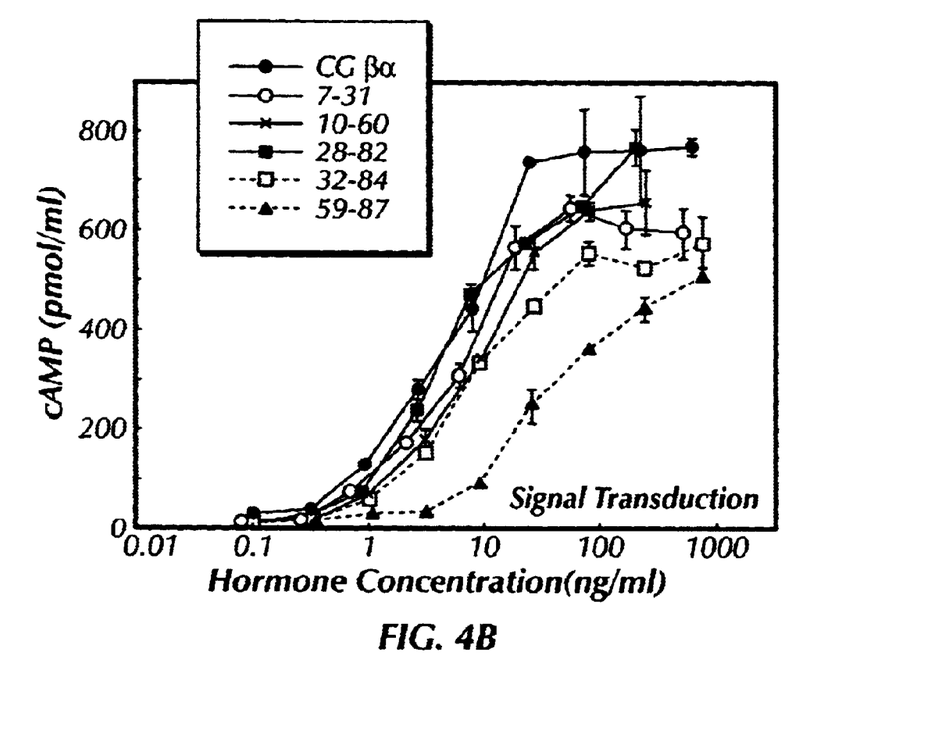

Biological activity both with respect to binding and signal transduction were measured as described for the analogous β cystine bridge deleted mutants in example 2. The results are shown in FIGS. 4a and 4b and tabulated in Table 4.

TABLE 4

Biological Activity of α Subunit Cystine-Depleted Mutants in CG Single Chain

| | Binding $IC_{50}$(ng/ml) | cAMP $ED_{50}$(ng/ml) | Coupling Factor $IC_{50}/ED_{50}$ |
|---|---|---|---|
| CGβα | 23.3 ± 7.9 | 4.3 ± 0.8 | 3.4 ± 1.4 |
| 7–31 | 6.7 ± 1.7 | 7.4 ± 1.8 | 1.0 ± 0.3 |
| 10–60 | 26.9 ± 8.4 | 11.9 ± 3.5 | 2.9 ± 1.2 |
| 28–82 | 6.5 ± 2.1 | 6.9 ± 0.5 | 1.0 ± 0.2 |
| 32–84 | 14.1 ± 3.1 | 12.9 ± 3.6 | 1.6 ± 0.6 |
| 59–87 | 254.3 ± 55.4 | 43.2 ± 15.5 | 8.1 ± 2.7 |

As shown, all of the mutants have significant binding and signal transduction activity. However, both properties of the α59–87 mutant were significantly reduced.

What is claimed is:

1. A modified form of a glycoprotein hormone selected from the group consisting of follicle stimulating hormone (FSH), luteinizing hormone (LH), chorionic gonadotropin (CG) and thyroid stimulating hormone (TSH) of the formula:

(β)–(linker)$_n$–α wherein β represents the β subunit of said FSH, LH, CG or TSH or a variant thereof;

α represents the α subunit common to said glycoprotein hormones or a variant thereof;

"linker" represents an amino acid sequence providing a fusion protein between the C-terminus of β and the N-terminus of α and n is 0 or 1;

wherein one cystine bridge contained in said α or β subunit is deleted wherein said bridge is selected from the group consisting of:

the 7–31 cystine link in the α chain;
the 10–60 cystine link in the α chain;
the 28–82 cystine link in the α chain;
the 32–84 cystine link in the α chain;
the 34–88 cystine link in the β chain;
the 38–90 cystine link in the β chain;
the 9–57 cystine link in the β chain;
the 23–72 cystine link in the β chain;
the 93–100 cystine link in the β chain; and
the 26–110 cystine link in the β chain,
wherein positions shown in β chain denote positions in the β chain of human CG or the analogous positions in LHβ, TSHβ or FSHβ;

and wherein said modified form is an agonist of said glycoprotein hormone.

2. The modified form of claim 1 wherein the deleted cystine bridge is in the α subunit.

3. The modified form of claim 1 wherein the deleted cystine bridge is in the β subunit.

4. A pharmaceutical or veterinary composition which comprises the modified form of claim 1 in admixture with a pharmaceutically acceptable excipient.

5. The modified form of claim 2 wherein said deleted cystine bridge is selected from the group consisting of:

the 10–60 cystine link in the α chain;
the 28–82 cystine link in the α chain; and
the 32–84 cystine link in the α chain.

6. The modified form of claim 3 wherein said deleted cystine bridge is selected from the group consisting of:

the 9–57 cystine link in the β chain;
the 23–72 cystine link in the β chain;
the 93–100 cystine link in the β chain; and
the 26–110 cystine link in the β chain.

7. The modified form of claim 5 wherein the deleted cystine bridge is the 10–60 cystine link in the α chain.

8. The modified form of claim 5 wherein the deleted cystine bridge is the 28–82 cystine link in the α chain.

9. The modified form of claim 5 wherein the deleted cystine bridge is the 32–84 cystine link in the α chain.

10. The modified form of claim 6 wherein said deleted cystine bridge is the 9–57 cystine link in the β chain.

11. The modified form of claim 6 wherein said deleted cystine bridge is the 23–72 cystine link in the β chain.

12. The modified form of claim 6 wherein said deleted cystine bridge is the 93–100 cystine link in the β chain.

13. The modified form of claim 6 wherein said deleted cystine bridge is the 26–110 cystine link in the β chain.

14. A pharmaceutical or veterinary composition which comprises the modified form of claim 2 in admixture with a pharmaceutically acceptable excipient.

15. A pharmaceutical or veterinary composition which comprises the modified form of claim 3 in admixture with a pharmaceutically acceptable excipient.

16. A pharmaceutical or veterinary composition which comprises the modified form of claim 5 in admixture with a pharmaceutically acceptable excipient.

17. A pharmaceutical or veterinary composition which comprises the modified form of claim 6 in admixture with a pharmaceutically acceptable excipient.

* * * * *